(12) United States Patent
Li et al.

(10) Patent No.: US 12,329,842 B2
(45) Date of Patent: Jun. 17, 2025

US012329842B2

(54) POLYMER COMBINATIONS TO IMPROVE FRAGRANCE LONGEVITY

(71) Applicant: ELC Management LLC, Melville, NY (US)

(72) Inventors: Geng Li, Brooklyn, NY (US); Jaime Manuel Ferreira, Park Ridge, NJ (US); Natalie Michelle Drucker, Lexington, KY (US)

(73) Assignee: ELC Management LLC, Melville, NY (US)

( * ) Notice: Subject to any disclaimer, the term of this patent is extended or adjusted under 35 U.S.C. 154(b) by 906 days.

(21) Appl. No.: 17/480,092

(22) Filed: Sep. 20, 2021

(65) Prior Publication Data

US 2023/0092772 A1   Mar. 23, 2023

(51) Int. Cl.
*A61K 8/73*   (2006.01)
*A61K 8/86*   (2006.01)
*A61K 8/87*   (2006.01)
*A61Q 13/00*   (2006.01)

(52) U.S. Cl.
CPC ................ *A61K 8/731* (2013.01); *A61K 8/86* (2013.01); *A61K 8/87* (2013.01); *A61Q 13/00* (2013.01); *A61K 2800/594* (2013.01)

(58) Field of Classification Search
CPC .......... A61Q 13/00; A61K 8/87; A61K 8/731; A61K 8/86; A61K 2800/594
USPC ........................................................ 512/2, 1
See application file for complete search history.

(56) References Cited

U.S. PATENT DOCUMENTS

2015/0011457 A1   1/2015   Seidling et al.

FOREIGN PATENT DOCUMENTS

| EP | 1545435 A2 * | 6/2005 | ............. A61K 8/731 |
| EP | 2800548 B1 | 2/2016 | |
| WO | WO 2004/030606 A2 | 4/2004 | |
| WO | WO-2016081714 A1 * | 5/2016 | ........... A61K 31/045 |

OTHER PUBLICATIONS

O'Halloran et al, EP 1545435 Machine Translation, Jul. 18, 2007 (Year: 2007).*
PCT International Search Report; International Application No. PCT/US2022/043916; Completion Date: Jan. 13, 2023; Mailing Date: Jan. 13, 2023; 20.58.
PCT Written Opinion of the International Searching Authority; International Application No. PCT/US2022/043916; Completion Date: Jan. 13, 2023; 20.58.
China International Search Report from CN Application No. 202280070827.2; Notice Date: Jul. 16, 2024; 20.58 (with English Translation).

\* cited by examiner

*Primary Examiner* — Jessica Whiteley
(74) *Attorney, Agent, or Firm* — Kirby Drake

(57) ABSTRACT

Polymer combinations may be incorporated in a hydroalcoholic solution to improve fragrance longevity. The polymer combination may include at least one plant-based hydrophobic polymer, a hydrophilic polymer, a third cosmetically acceptable sensory polymer, and a fragrance oil in hydroalcoholic solution having prolonged fragrance intensity. The tri-polymer combination may synergistically create a film mesh on the surface of the skin that locks in the fragrance ingredients. The combination may provide an unexpected film forming property with the fragrance oil in hydroalcoholic solution, thereby providing a thin film matrix and adhesive power for the fragrance ingredients to attach/remain on the skin.

18 Claims, 3 Drawing Sheets

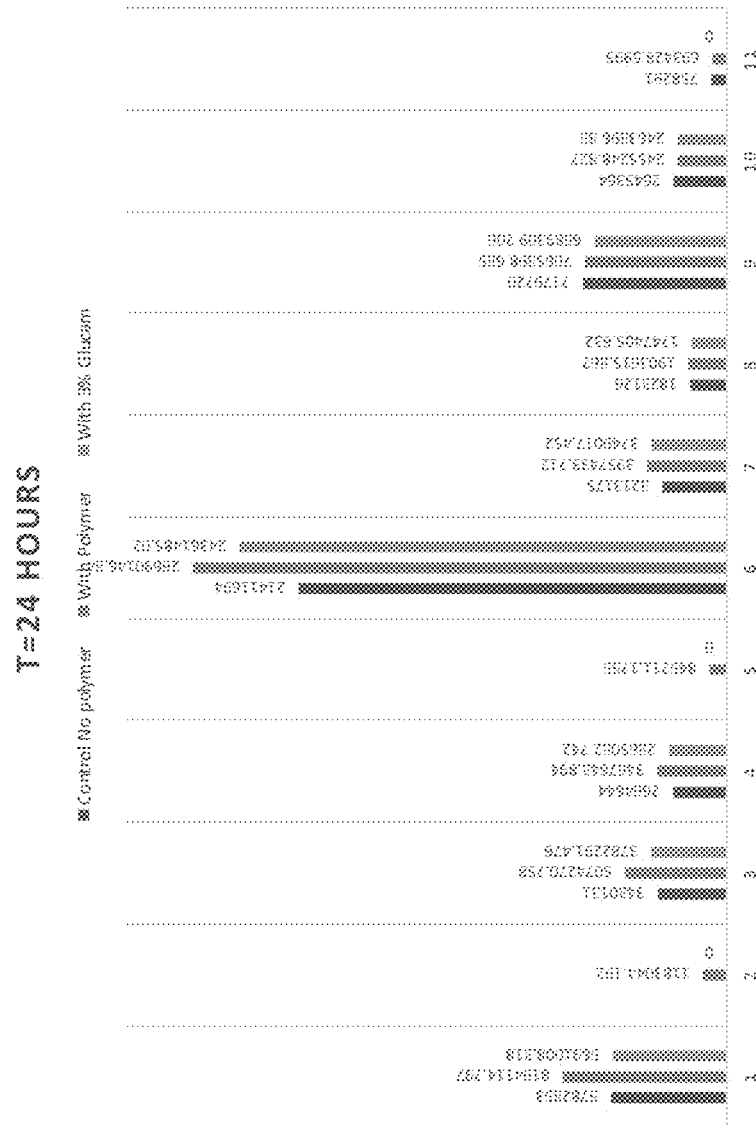

POLYMER COMBINATIONS TO IMPROVE FRAGRANCE LONGEVITY

FIELD OF THE DISCLOSURE

The present disclosure generally relates to fragrance longevity, and more particularly to polymer combinations in a hydroalcoholic solution that improve fragrance longevity.

BACKGROUND

Many fragrance wearers complain that fragrances do not last on them, and they may conclude that they did not apply enough fragrance. The concentration of the fragrance also may affect fragrance longevity, as typically the more alcohol that is present in the fragrance, the faster it may lose its scent. In general, wearers want a fragrance to have a long-lasting effect over time when applied to a wearer's skin without requiring additional applications.

SUMMARY

Embodiments of the present disclosure may provide a system that improves fragrance longevity, the system comprising: a polymer combination comprising at least one plant-based hydrophobic polymer, a hydrophilic polymer, and a third cosmetically acceptable sensory polymer; and a fragrance oil in a hydroalcoholic solution, wherein the polymer combination creates a film mesh on a surface of skin that locks in the fragrance oil to improve fragrance longevity. The at least one plant-based hydrophobic polymer may be ethylcellulose. Ethylcellulose may be present as 0.01-7.00% of the system. The at least one plant-based hydrophobic polymer may be selected from the group consisting of: ethylcellulose, hydroxyethylcellulose, hydroxypropyl methylcellulose, and/or carboxymethylcellulose (cellulose gum). The hydrophilic polymer may be poloxamer 407 and PPG-12/SMDI copolymer. Poloxamer 407 and PPG-12/SMDI copolymer may be present as 0.01-5.00% of the system. The hydrophilic polymer may be selected from the group consisting of: poloxamer 407 and PPG-12/SMDI copolymer, poloxamer 338 and PPG-12/SMDI copolymer, PPG-17/IPDI/DMPA copolymer, poloxamer 407, poloxamer 338, and/or poloxamer 184. The third cosmetically acceptable sensory polymer may be polyurethane-1. Polyurethane-1 may be present as 0.005% to 5% of the system. The third cosmetically acceptable sensory polymer may be selected from the group consisting of: polyurethane-1, polyurethane-18, polyurethane-34, polyurethane-35, polyurethane-48, polyurethane-64, polyurethane-21, PPG-12/SMDI Copolymer, PPG-51/SMDI Copolymer, and/or PPG-8/SMDI Copolymer. The fragrance oil in a hydroalcoholic solution may comprise 5-95% ethanol, 0-25% water, and 0.1-25% fragrance oil with a c Log P of 0.7-7.0. The fragrance oil level may be at least 0.5% of the system.

Other embodiments of the present disclosure may provide a system that improves fragrance longevity, the system comprising: a polymer combination comprising ethylcellulose, poloxamer 407 and PPG-12/SMDI, and polyurethane-1; and a fragrance oil in a hydroalcoholic solution, wherein the polymer combination creates a film mesh on a surface of skin that locks in the fragrance oil to improve fragrance longevity. The polymer combination may comprise 0.75% of the system, ethylcellulose may comprise 0.45% of the system, poloxamer 407 and PPG-12/SMDI copolymer may comprise 0.29% of the system, and polyurethane-1 may comprise 0.01% of the system. The polymer combination may comprise 0.5% of the system, ethylcellulose may comprise 0.45% of the system, poloxamer 407 and PPG-12/SMDI copolymer may comprise 0.04% of the system, and polyurethane-1 may comprise 0.01% of the system. The polymer combination may comprise 1% of the system, ethylcellulose may comprise 0.50% of the system, poloxamer 407 and PPG-12/SMDI copolymer may comprise 0.49% of the system, and polyurethane-1 may comprise 0.01% of the system. The polymer combination may comprise 1.46% of the system, ethylcellulose may comprise 0.95% of the system, poloxamer 407 and PPG-12/SMDI copolymer may comprise 0.50% of the system, and polyurethane-1 may comprise 0.01% of the system.

Additional embodiments of the present disclosure may provide a system that improves fragrance longevity, the system comprising: a polymer combination comprising at least one plant-based hydrophobic polymer present in a range of 0.01-7.00% of the system, a hydrophilic polymer present in a range of 0.01-5.00% of the system, and a third cosmetically acceptable sensory polymer present in a range of 0.005% to 5% of the system; and a fragrance oil in a hydroalcoholic solution, the fragrance oil having a c Log P of 0.7-7.0, wherein the polymer combination creates a film mesh on a surface of skin that locks in the fragrance oil to improve fragrance longevity. The at least one plant-based hydrophobic polymer may be ethylcellulose, the hydrophilic polymer may be poloxamer 407 and PPG-12/SMDI copolymer, and the third cosmetically acceptable sensory polymer may be polyurethane-1. The fragrance oil level is at least 0.5% of the system.

BRIEF DESCRIPTION OF THE DRAWINGS

For a more complete understanding of this disclosure, reference is now made to the following description, taken in conjunction with the accompanying drawings, in which:

FIG. 2 depicts results of the headspace GS/MS peak intensities both including and without the polymer combinations.

DETAILED DESCRIPTION

Embodiments of the present disclosure may provide polymer combinations in a hydroalcoholic solution that improve fragrance longevity. The polymer combination may include at least one plant-based hydrophobic polymer, a hydrophilic polymer, a third cosmetically acceptable sensory polymer, and a fragrance oil in hydroalcoholic solution to provide prolonged fragrance intensity.

Figure 1B:
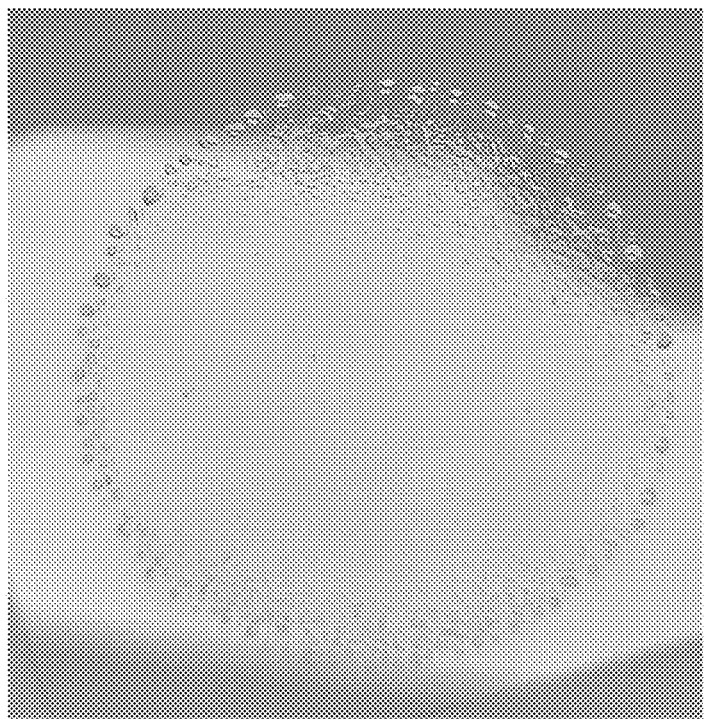
FIGS. 1A-1B depict glass slides having a drop of a sample including and without the polymer combination according to an embodiment of the present disclosure.
Figure 1A:
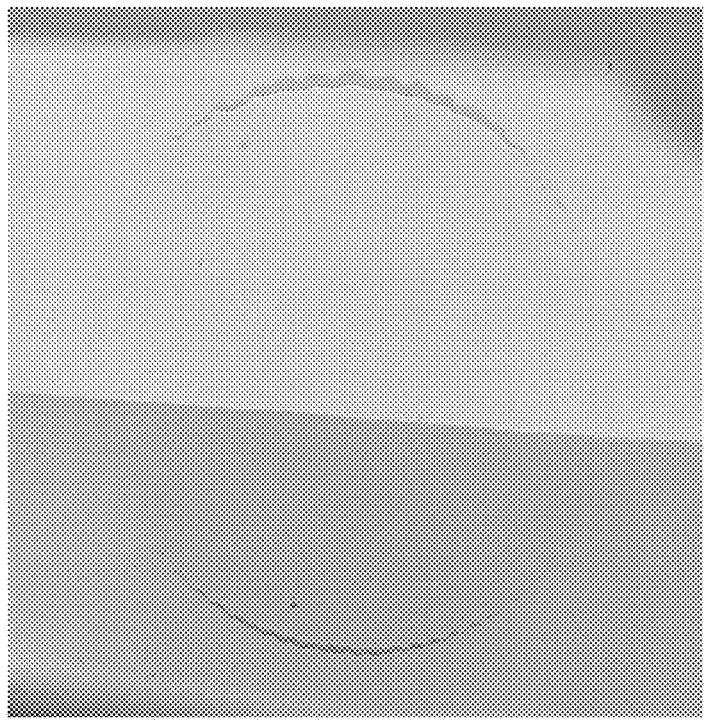

This combination of polymers according to embodiments of the present disclosure may leverage transfer-resistant film former technology with food and medical grade polymers. The tri-polymer combination may synergistically create a film mesh on the surface of the skin that locks in the fragrance ingredients. The polymer combination may provide an unexpected film forming property with the fragrance oil in hydroalcoholic solution, thereby providing a thin film matrix and adhesive power for the fragrance ingredients to attach/remain on the skin. This film forming property is reflected in FIGS. 1A-1B which depict glass slides having a drop of a sample including and without the polymer combination.

In an embodiment of the present disclosure, the at least one plant-based hydrophobic polymer may be Ethocel Standard 45 Premium manufactured by DuPont (INCI name: ethylcellulose). Ethylcellulose is a plant-based polymer utilized in cosmetic compositions as a film-forming agent (i.e., facilitating the formation of a film on the skin and improving the water resistance of the film) and may be present as 0.01-7.00% of the total composition. Other plant-based hydrophobic polymers that may be used in addition to or in place of ethylcellulose may include Celopre® H30000 manufactured by Celotech Chemical Co., Ltd., Natrosol™ 250 HHR Hydroxyethylcellulose, PC Grade manufactured by Ashland, Hydroxyethyl Cellulose, 100 CP, NF (HY112) manufactured by Spectrum Chemical Mfg. Corp., HEC CF-G or HEC CF-V manufactured by Sumitomo Seika Chemicals Co., Ltd., and/or Vida-Care HEC manufactured by Univar Solutions (each of which having INCI name: hydroxyethylcellulose). Additional plant-based hydrophobic polymers may include Celopre® ME30M manufactured by Celotech Chemical Co., Ltd., Benecel™ E4M polymer manufactured by Ashland, and/or PrimaFlo™ MP3295A polymer manufactured by Ashland (each of which having INCI name: hydroxypropyl methylcellulose). Other plant-based hydrophobic polymers may include GELYCEL® manufactured by Quimica Amtex y Amtex Chemicals, LLC, Carboxymethylcellulose Sodium, Low Viscosity (CA193) manufactured by Spectrum Chemical Mfg. Corp., and/or Carboxymethylcellulose Sodium, Medium Viscosity (CA192) manufactured by Spectrum Chemical Mfg. Corp. (each of which having INCI name: carboxymethylcellulose (cellulose gum)).

A hydrophilic polymer utilized in polymer combinations according to embodiments of the present disclosure may be ExpertGel® EG412 manufactured by DKSH North America, Inc. (INCI name: poloxamer 407 and PPG-12/SMDI copolymer), which is a film-forming agent to enhance texture in cosmetic products. This polymer may have a thermosetting property based on skin temperature and may be present as 0.01-5.00% of the total composition. Other hydrophilic polymers may include ExpertGel® EG 312 manufactured by DKSH North America Inc. (INCI name: poloxamer 338 and PPG-12/SMDI copolymer), Avalure® UR 450 Polymer manufactured by Lubrizol (INCI name: PPG-17/IPDI/DMPA copolymer), Pluracare® F 127 NF Prill FLEX or Pluracare® F 127 NF Prill manufactured by BASF Care Creations or ANTAROX® F 127 NF manufactured by Solvay Novecare (each of which having INCI name: poloxamer 407), Pluracare® F 108 NF Prill (INCI name: poloxamer 338), and/or Pluracare® L 64 manufactured by BASF Care Creations (INCI name: poloxamer 184).

A third cosmetically acceptable sensory polymer utilized in polymer combinations according to embodiments of the present disclosure may be LUVISET® P.U.R. manufactured by BASF (INCI name: polyurethane-1) in the range of 0.005% to 5% of the total composition. Polyurethane-1 is a copolymer of isophthalic acid monomers, adipic acid, hexylene glycol, neopentyl glycol, dimethylolpropanic acid and isophorone diisocyanate. This polymer may be able to form a film and may release active agents at the level of the skin. A polymer may be characterized as a cosmetically acceptable sensory polymer as it may have a non-tacky, draggy feel. Other cosmetically acceptable sensory polymers may include Polyderm PE/PA manufactured by ALZO International Inc. (INCI name: polyurethane-18), Baycusan® C 1000 or Baycusan® C 1001 manufactured by Covestro (INCI name: polyurethane-34), Baycusan® C 1004 manufactured by Covestro (INCI name: polyurethane-35), Baycusan® C 1008 or Baycusan® C 1008/1 manufactured by Covestro (INCI name: polyurethane-48), Baycusan® C 2000 manufactured by Covestro (INCI name: polyurethane-64), GIOVAREZ® P-0580 manufactured by Phoenix Chemical, Inc. (INCI name: polyurethane-21), Polyolprepolymer-2 (INCI name: PPG-12/SMDI Copolymer), Polyolprepolymer-14 (INCI name: PPG-51/SMDI Copolymer), and/or Polyolprepolymer-15 (INCI name: PPG-8/SMDI Copolymer) from Barnet Products Corporation. While polyurethane-1 and ethylcellulose may each individually be known to be used as contributors in fragrance and to fragrance longevity, embodiments of the present disclosure utilize them in combination with the hydrophilic polymer to bring increased levels of fragrance longevity.

The fragrance oil in hydroalcoholic solution in embodiments of the present disclosure may be comprised of at least 5-95% ethanol, 0-25% water, and 0.1-25% fragrance oil with a c Log P of 0.7-7.0. In an embodiment of the present disclosure, a fragrance hydroalcoholic homogenous solution may have a fragrance oil level of at least 0.5%, thereby incorporating higher amounts of fragrance oils. Inclusion of the polymer combinations according to embodiments of the present disclosure with a fragrance oil in hydroalcoholic solution may provide a sprayable thin form of homogenous hydroalcoholic solution. Stabilizers and/or other cosmetically acceptable dyes and combinations also may be included in embodiments of the present disclosure. Stabilizers, whether incorporated individually or in combination, may include COVABSORB® (INCI name: Ethylhexyl Methoxycinnamate (and) Butyl Methoxydibenzoylmethane (and) Ethylhexyl Salicylate), TINOGARD® Q (INCI name: Tris(Tetramethylhydroxypiperidinol) Citrate (and) Aqua (and) Alcohol), PARSOL 1789 (INCI name: Butyl Methoxydibenzoylmethane), and/or other commonly used antioxidants in a range of 0.005-2.0% of the total composition. Dyes may include one or more of the following: D452/4 EXT D&C VIOLET NO.2, D424/1 FD&C BLUE NO.1, S260/1 FD&C RED #33, d435/1 FD&C RED NO.4, and/or D436/1 FD&C YELLOW NO.5.

It should be appreciated that the ratios of the three types of polymers in the polymer combination may vary in embodiments of the present disclosure depending on the percentage of the total composition that the polymers comprise. In a first embodiment of the present disclosure, when the polymer combination comprises 0.75% of the total composition, ethylcellulose may comprise 0.45%, poloxamer 407 and PPG-12/SMDI copolymer may comprise 0.29%, and polyurethane-1 may comprise 0.01%. In another embodiment of the present disclosure, when the polymer combination comprises 0.5% of the total composition, ethylcellulose may comprise 0.45%, poloxamer 407 and PPG-12/SMDI copolymer may comprise 0.04%, and polyurethane-1 may comprise 0.01%. In a further embodiment of the present disclosure, when the polymer combination comprises 1% of the total composition, ethylcellulose may comprise 0.50%, poloxamer 407 and PPG-12/SMDI copolymer may comprise 0.49%, and polyurethane-1 may comprise 0.01%. In an additional embodiment of the present disclosure, when the polymer combination comprises 1.46% of the total composition, ethylcellulose may comprise 0.95%, poloxamer 407 and PPG-12/SMDI copolymer may comprise 0.50%, and polyurethane-1 may comprise 0.01%. It should be appreciated that the polymer alternatives described above may be incorporated into the polymer combinations in similar percentages based on the ratios described herein.

While embodiments of the present disclosure have been described with 0.1-25% fragrance oil with a c Log P of 0.7-7.0, it should be appreciated that fragrance oils having different c Log P values, and/or the composition and/or the total polymer level may have dramatic effects on the compatibility, stability, and skin feel. For instance, the polymer combination P=1.46% was observed to precipitate out from the solution at low temperature after 3 days in the fragrance oil with lower c Log P (e.g., 3.13), but precipitation was not observed for fragrance oil having a high c Log P (e.g., 3.8). Higher level of polymers, particularly ethylcellulose, may compromise the skin feel.

Figure 3:
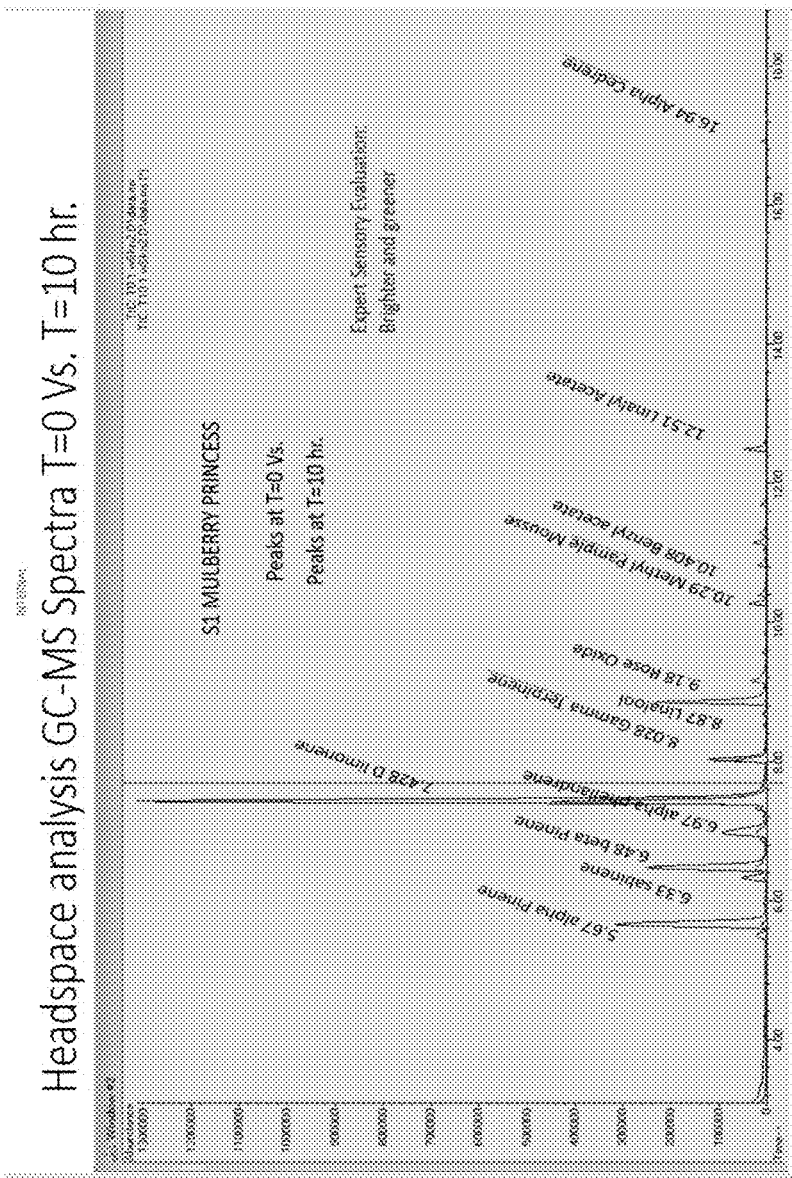
FIG. 3 depicts headspace GC/MS analysis spectra from 0 to 10 hours.

Headspace gas chromatography/mass spectrometry (GC/MS) was used to analyze and compare fragrance formulations both including and without polymer combinations according to embodiments of the present disclosure. FIG. 2 depicts results of the headspace GS/MS peak intensities both including and without the polymer combinations, reflecting that inclusion of the polymer combination improved the overall retention effect for fragrance ingredients. FIG. 3 depicts headspace GC/MS analysis spectra from 0 to 10 hours for a Mulberry Princess fragrance composition.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A system that improves fragrance longevity, the system comprising:
a polymer combination comprising at least one plant-based hydrophobic polymer, a hydrophilic polymer which is poloxamer 407 and PPG-12/SMDI copolymer, and a third cosmetically acceptable sensory polymer; and
a fragrance oil in a hydroalcoholic solution,
wherein the polymer combination creates a film mesh on a surface of skin that locks in the fragrance oil to improve fragrance longevity.

2. The system of claim 1 wherein the at least one plant-based hydrophobic polymer is ethylcellulose.

3. The system of claim 2 wherein ethylcellulose is present as 0.01-7.00% of the system.

4. The system of claim 1 wherein the at least one plant-based hydrophobic polymer is selected from the group consisting of:
ethylcellulose, hydroxyethylcellulose, hydroxypropyl methylcellulose, and/or carboxymethylcellulose (cellulose gum).

5. The system of claim 1 wherein poloxamer 407 and PPG-12/SMDI copolymer is present as 0.01-5.00% of the system.

6. The system of claim 1 wherein the third cosmetically acceptable sensory polymer is polyurethane-1.

7. The system of claim 6 wherein polyurethane-1 is present as 0.005% to 5% of the system.

8. The system of claim 1 wherein the third cosmetically acceptable sensory polymer is selected from the group consisting of:
polyurethane-1, polyurethane-18, polyurethane-34, polyurethane-35, polyurethane-48, polyurethane-64, polyurethane-21, PPG-12/SMDI Copolymer, PPG-51/SMDI Copolymer, and/or PPG-8/SMDI Copolymer.

9. The system of claim 1, the fragrance oil in a hydroalcoholic solution comprising:
5-95% ethanol, 0-25% water, and 0.1-25% fragrance oil with a c Log P of 0.7-7.0.

10. The system of claim 1, wherein the fragrance oil level is at least 0.5% of the system.

11. A system that improves fragrance longevity, the system comprising:
a polymer combination comprising ethylcellulose, poloxamer 407 and PPG-12/SMDI, and polyurethane-1; and
a fragrance oil in a hydroalcoholic solution,
wherein the polymer combination creates a film mesh on a surface of skin that locks in the fragrance oil to improve fragrance longevity.

12. The system of claim 11 wherein when the polymer combination comprises 0.75% of the system, ethylcellulose comprises 0.45% of the system, poloxamer 407 and PPG-12/SMDI copolymer comprises 0.29% of the system, and polyurethane-1 comprises 0.01% of the system.

13. The system of claim 11 wherein when the polymer combination comprises 0.5% of the system, ethylcellulose comprises 0.45% of the system, poloxamer 407 and PPG-12/SMDI copolymer comprises 0.04% of the system, and polyurethane-1 comprises 0.01% of the system.

14. The system of claim 11 wherein when the polymer combination comprises 1% of the system, ethylcellulose comprises 0.50% of the system, poloxamer 407 and PPG-12/SMDI copolymer comprises 0.49% of the system, and polyurethane-1 comprises 0.01% of the system.

15. The system of claim 11 wherein when the polymer combination comprises 1.46% of the system, ethylcellulose comprises 0.95% of the system, poloxamer 407 and PPG-12/SMDI copolymer comprises 0.50% of the system, and polyurethane-1 comprises 0.01% of the system.

16. A system that improves fragrance longevity, the system comprising:
a polymer combination comprising at least one plant-based hydrophobic polymer present in a range of 0.01-7.00% of the system, a hydrophilic polymer present in a range of 0.01-5.00% of the system, and a third cosmetically acceptable sensory polymer present in a range of 0.005% to 5% of the system; and
a fragrance oil in a hydroalcoholic solution, the fragrance oil having a c Log P of 0.7-7.0,
wherein the polymer combination creates a film mesh on a surface of skin that locks in the fragrance oil to improve fragrance longevity.

17. The system of claim 16 wherein the at least one plant-based hydrophobic polymer is ethylcellulose, the hydrophilic polymer is poloxamer 407 and PPG-12/SMDI copolymer, and the third cosmetically acceptable sensory polymer is polyurethane-1.

18. The system of claim 16, wherein the fragrance oil level is at least 0.5% of the system.

* * * * *